(12) United States Patent
Rebstock et al.

(10) Patent No.: US 8,206,408 B2
(45) Date of Patent: Jun. 26, 2012

(54) SURGICAL INSTRUMENT WITH A SHAFT HAVING A SLIDING PART

(75) Inventors: Dieter Rebstock, Duerbheim-Tuttlingen (DE); Rudolf Rebstock, Duerbheim-Tuttlingen (DE)

(73) Assignee: Rebstock Instruments GmbH, Duerbheim-Tuttlingen (DE)

( * ) Notice: Subject to any disclaimer, the term of this patent is extended or adjusted under 35 U.S.C. 154(b) by 169 days.

(21) Appl. No.: 12/707,118

(22) Filed: Feb. 17, 2010

(65) Prior Publication Data

US 2010/0222800 A1 Sep. 2, 2010

(30) Foreign Application Priority Data

Feb. 20, 2009 (DE) .................... 20 2009 002 433 U
Feb. 3, 2010 (DE) ......................... 10 2010 006 846

(51) Int. Cl.
*A61B 17/32* (2006.01)

(52) U.S. Cl. ............. 606/167; 606/79; 606/83; 606/170

(58) Field of Classification Search .................. 606/79, 606/83, 167–180, 205, 206
See application file for complete search history.

(56) References Cited

U.S. PATENT DOCUMENTS

| | | | |
|---|---|---|---|
| 5,484,441 A | 1/1996 | Koros et al. | |
| 5,961,531 A | 10/1999 | Weber et al. | |
| 6,126,674 A | 10/2000 | Janzen | |
| 6,520,979 B1 * | 2/2003 | Loubens et al. | ............. 606/205 |
| 2003/0088268 A1 | 5/2003 | Weinmann | |
| 2006/0122615 A1 | 6/2006 | McKinley | |

FOREIGN PATENT DOCUMENTS

| | | |
|---|---|---|
| DE | 201 03 630 U1 | 1/2001 |
| EP | 1 092 397 B1 | 10/2000 |

OTHER PUBLICATIONS

Search Report for Parent DE 20 2009 002 433.4 (German 4 pages); and Translation of same in English (5 pages).

* cited by examiner

*Primary Examiner* — Tuan Nguyen
(74) *Attorney, Agent, or Firm* — Andrew F. Young, Esq.; Lackenbach Siegel, LLP

(57) ABSTRACT

A surgical instrument having a shaft with a fixed handle part having a sliding part arranged thereon, and axially movable by means of a pivotable handle. The sliding part is guided on the shaft within an axial working stroke by proximal and distal guidance mechanism. A locking mechanism limit the axial displacement of the sliding part on the proximal end of the working stroke. In use, after unlocking the locking mechanism. the sliding part is movable beyond the proximal end of the working stroke into a cleaning position, in which the distal guidance mechanism are disengaged, so that the sliding part can be lifted away from the shaft.

18 Claims, 8 Drawing Sheets

C-C

D-D

SURGICAL INSTRUMENT WITH A SHAFT HAVING A SLIDING PART

CROSS REFERENCE TO RELATED APPLICATIONS

This application relates to and claims priority from German Patent Application Serial No. 20 2009 002 433.4, filed Feb. 20, 2009 the entire contents of which is herein incorporated fully by reference. This application additionally relates to and claims priority from German Patent Application Ser. No. 20 2010 006 846.2, filed Feb. 3, 2010 having similar content, the contents of which is also incorporated herein by reference.

FIGURE FOR PUBLICATION

FIG. 1.

BACKGROUND OF THE INVENTION

1. Field of the Invention

The present invention relates to sliding shaft surgical instruments. More specifically, the present invention relates to a sliding shaft surgical instrument with an improved guidance means for guiding the sliding shaft and detaching the sliding portion for ease of cleaning.

2. Description of the Related Art

The related art involves surgical instruments of this generic type which are also known as sliding shaft instruments which have a shaft with a stationary handle part. A sliding part, which is axially displaceable by means of a pivotable handle part, is guided on the shaft. Working elements, which can be operated by the axial displacement of the sliding part, are arranged on the distal end of the shaft and of the sliding part. If the instrument is designed as a punch, for example, then cutting edges are formed on the distal end of the shaft and of the sliding part, these cutting edges being moved by the axial movement of the sliding part to sever tissue, cartilage, bone or the like.

Distal and proximal guidance means, which guide the sliding part in a sliding plane on the shaft within an axial working stroke for actuation of the working element, are provided for guiding the sliding part on the shaft. In this process, the axial displacement of the sliding part is limited at the proximal end of the working stroke by locking means, so that the distal and proximal guidance means remain engaged while the instrument is in use and keep the sliding part guided on the shaft. The locking means may be unlocked, so that the sliding part is movable into a cleaning position in the proximal direction beyond the limited working stroke. In this cleaning position, the guidance means are disengaged, so the sliding part can be lifted away from the shaft to be able to thoroughly clean and sterilize the instrument.

There are known instruments with which the sliding part is completely separated from the remaining instrument in the cleaning position (e.g., DE 201 03 630 U1). With other instruments, however, the sliding part is connected to the remaining instrument, but cannot be pivoted away from the shaft. However, in the case of an instrument known from EP 1 092 397 B1, which issued Dec. 7, 2005, to Tontarra for a Surgical Instrument, the sliding part is connected to the pivotable handle part on its proximal end. In the case of an instrument known from U.S. Pat. No. 5,961,531, which issued Oct. 5, 1999, to Weber et al. for a Convertible Rongeur, the sliding part is connected by an pivot pin to the stationary instrument part by means of a connecting piece. Locking means are known in a wide variety of embodiments, e.g., from U.S. Pat. No. 6,126,674, US 2003/0088268 A1 and EP 1 092 397 B1.

With the known instruments, the distal guidance means and the proximal guidance means each have a guidance web having a T-shaped cross-sectional profile running axially, engaging with a corresponding T-shaped cross-sectional profile in the area of the working stroke in a guidance groove. In the cleaning position, the guidance webs emerge from the guidance grooves in the proximal direction, so that they can be lifted out of these guidance grooves to lift the sliding part away from the shaft. The guidance webs and the undercut guidance grooves are complex to manufacture. The undercut T-shaped guidance grooves also make cleaning of the instrument difficult.

What is not appreciated by the prior art is the need for simpler, more cost effective manufacturing of sliding shaft surgical instruments. Additionally, there is a need for a sliding shaft surgical instrument that is more easily cleaned and serviced.

Accordingly, there is a need for an improved surgical instrument which will permit simpler fabrication and cleaning.

ASPECTS AND SUMMARY OF THE INVENTION

An aspect of the present invention is to provide an inventive surgical instrument, which will permit simpler fabrication and cleaning.

The inventive surgical instrument, which is designed as a punch, for example, corresponds essentially to traditional instruments. This relates in particular to the design of the handle parts for actuation of the instrument, the design of the distal working elements and the design of the shaft and the sliding part. The design of the distal guidance means may correspond to that of traditional instruments. In particular, the distal guidance means may have a guidance web with a T-shaped cross-sectional profile, which is guided in a guidance groove having a corresponding T-shaped cross-sectional profile. Through these distal guidance means, the sliding part and the shaft are guided precisely in the distal region, so that the working elements are moved accurately in relation to one another in the working stroke, as is required for a precision surgical instrument.

The inventive instrument differs from the instruments known in the state of the art essentially in the design of the proximal guidance means. These proximal guidance means have two walls, which are arranged on the two exteriors of the shaft and of the sliding part, and which induce the lateral guidance of the sliding part on the shaft. The walls are preferably arranged on the shaft and the sliding part is guided to slide between these walls. However, it is also possible to bring the walls to the sliding part, so that the sliding part can glide on the shaft guided with these walls. To keep the sliding part in contact with the shaft, a link slot is formed in each of the walls, a pin of the other part, e.g., a pin of the sliding part, engaging in the link slot when the walls are formed on the shaft. The link slots have a guidance section running parallel to the sliding plane of the shaft and the sliding part. In this guidance section, the pin moves when the sliding part is in the axial displacement area of the working stroke. The distance of the guidance sections from the sliding plane of the shaft and of the sliding part and the distance of the pins from this sliding plane are selected, so that the sliding part and the shaft are in contact with one another in the sliding plane when the pins each move in the guidance sections of the link slots.

The guidance section of the link slots each develop into an end section. When the locking means are unlocked and the sliding part moves proximally into the cleaning position, the pins each enter the end section of the respective link slot. The end section is designed so that it allows lifting of the proximal end of the sliding part away from the shaft. If the end section of the link slot is open, then the pins can emerge out of the link slots in the proximal movement of the sliding part into the cleaning position, so that the sliding part is completely separated from the shaft and the remaining instrument and can be removed. However, in a preferred embodiment, the end section of the link slot is closed and angles away from the sliding plane. If the pins enter this end section, this lifts the sliding part away from the shaft, but the sliding part remains connected to the shaft and the remaining instrument via the walls and the pins. The sliding part may be pivoted about the pins as a pivot axis, so the distal end of the sliding part can be pivoted away from the shaft.

The proximal guidance means consisting of the lateral walls and the pins engaging in their link slots are simpler to manufacture in terms of fabrication technology than the T-shaped guidance webs and the undercut guidance grooves of the known instruments. This sliding part and the shaft are in contact with one another in the proximal area and in particular in the area of the proximal guidance means having smooth sliding planes, which can be cleaned easily and reliably.

The above, and other aspects, features and advantages of the present invention will become apparent from the following description read in conduction with the accompanying drawings, in which like reference numerals designate the same elements.

DETAILED DESCRIPTION OF THE PREFERRED EMBODIMENTS

Figure 1:
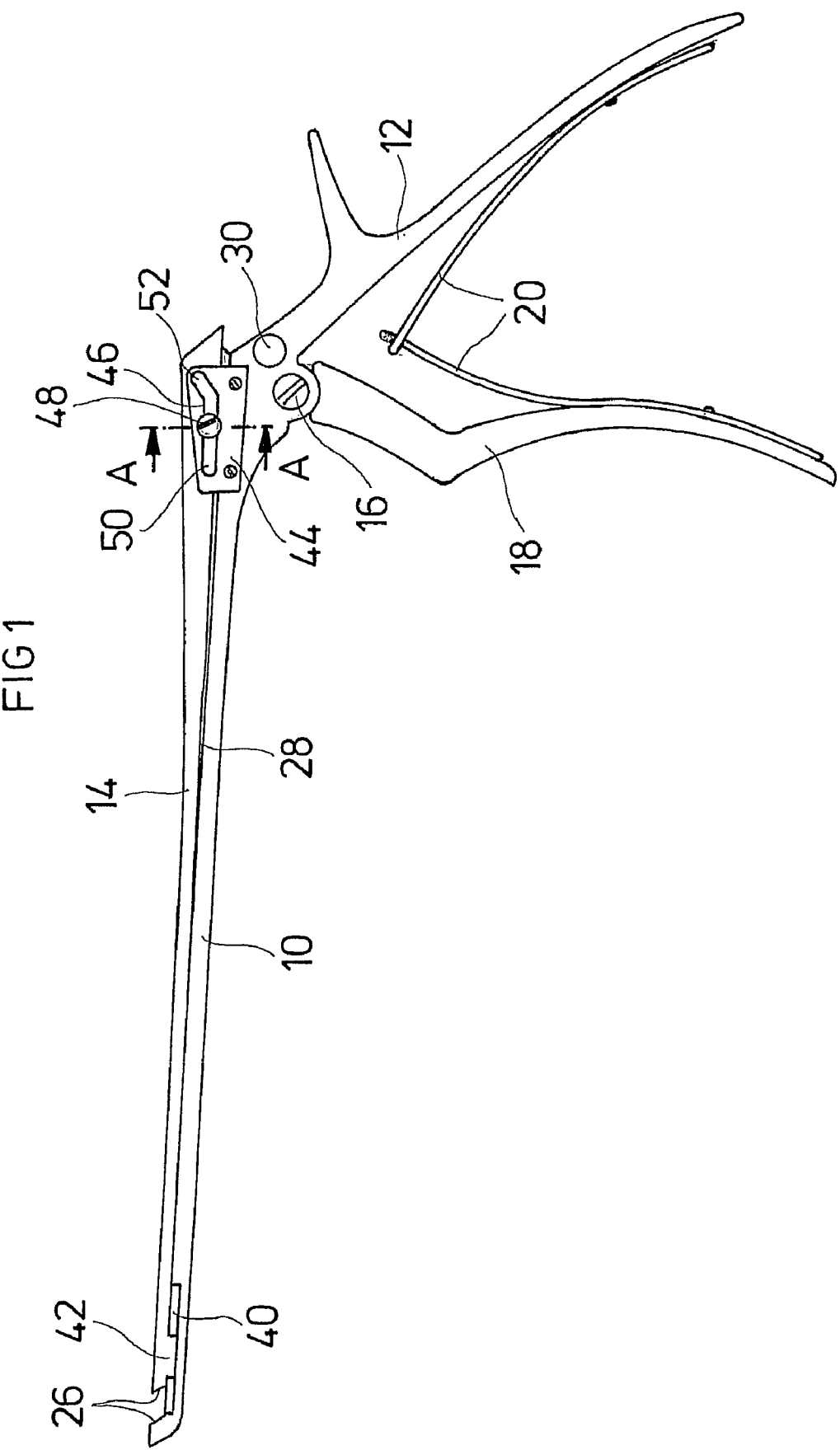
FIG. 1 shows a side view of an instrument designed as a punch in the working position.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

In the exemplary embodiment shown here, the surgical instrument is designed as a punch and/or rongeur. Modifications of the sliding shaft instrument for other intended uses, e.g., as tongs or the like, will be readily apparent to those skilled in the art.

The instrument has a shaft 10, the proximal end of which has a fixed handle part 12 designed in one piece and angled in relation to the longitudinal axis of the shaft 10. A sliding part 14, which is axially displaceable with respect to the shaft 10, is arranged on the shaft 10 and in contact with it. On the proximal end of the shaft 10 and/or the fixed handle part 12, a pivotable handle part 18 is mounted to pivot about a pivot pin 16, which is designed as a lock screw, for example. An expanding spring 20 which pivot the pivotable handle part 18 away from the fixed handle part 12 is mounted between the fixed handle part 12 and the pivotable handle part 18. The end of the pivotable handle part 18 protruding beyond the pivot pin 16 on the shaft end is designed like a fork with a notch 22. With this notch 22, the shaft end of the pivotable handle part 18 on the shaft end surrounds a driving pin 24, which passes transversely through a chamfer on the proximal end of the sliding part 14. By pivoting the handle part 18 toward the fixed handle part 12, the sliding part 14 can be advanced axially on the shaft 10 in this way. Working means are formed on the distal end of the shaft 10 and the sliding part 14. In the exemplary embodiment of a punch shown here, the working elements on the distal end of the shaft 10 and on the distal end of the sliding part 14 are cutting edges 26 that can be moved in relation to one another.

To this extent, the instrument has a traditional design, and those skilled in the art will be aware of structural details from the prior art.

The sliding part 14 is longitudinally displaceably guided on the shaft 10 by means of distal and proximal guidance means. The sliding part 14 here is guided on the shaft 10 and in contact with it in a sliding plane 28 within an axial working stroke. The axial working stroke is bordered in the distal direction by the fact that the cutting edges 26 of the sliding part 14 and of the shaft 10 come in contact with one another. In the proximal direction, the working stroke is limited by locking means. These locking means limit either the pivot angle of the pivotable handle part 18 or the proximal displacement path of the sliding part 14. Such locking means are known from the prior art in various embodiments.

Figure 7:
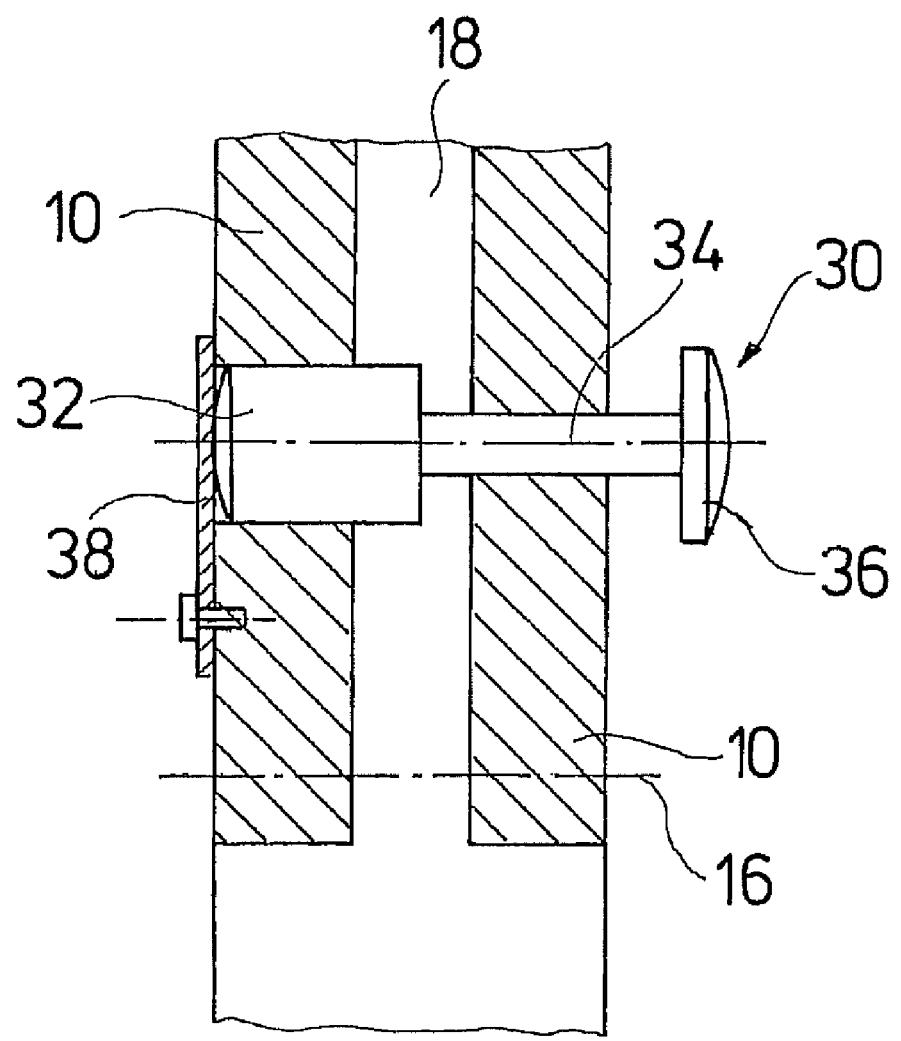
FIG. 7 shows a cross section through the locking means according to section C-C in FIG. 2.

In the exemplary embodiment shown here, the locking means consist in particular of a locking pin 30, which is shown in detail in FIG. 7. The locking pin 30 passes transversely displaceably through the fixed handle part 12 proximally behind the end of the pivotable handle part 18 protruding above the pivot pin 16 on the shaft end. The locking pin 30 therefore limits the pivoting movement of the end of the pivotable handle part 18, which passes through the fixed handle part 12, in the proximal direction when this pivotable handle part 18 is spread apart by the expanding spring 20 away from the fixed handle part 12. The locking pin 30 has an axial section 32 with a larger diameter and an axial section 34 with a smaller diameter. At the end of the axial section 34 having the smaller diameter, a widened pushbutton 36 is arranged. A plate spring 38 mounted on the fixed handle part 12 is in spring contact with the end of the axial section 32 having the larger diameter and presses the locking pin 30 into the locking position shown in FIG. 7. In this locking position, the axial section 32 of the locking pin 30 having the larger diameter comes into the pivot path of the pivotable handle part 18, so that the pivoting movement of the pivotable handle part 18 is limited by coming to a stop against the circumference of the section 32 having the larger diameter. The locking pin 30 can be unlocked from this locking position by displacing the locking pin 30 against the force of the plate spring 38 by means of the pushbutton 36 (toward the left in FIG. 7). The axial section 32 having the larger diameter therefore leads out of the pivot area of the pivotable handle part 18 in the transverse direction, and only the axial section 34 having the smaller diameter is in the pivot path of the pivotable handle part 18. According to the smaller diameter of the locking pin 30 in this section 34, the pivotable handle part 18 can now pivot further under the influence of the expanding spring 20 until the end of the pivotable handle part 18 protruding beyond the pivot pin 16 on the shaft end comes to a stop on the circumference of the locking pin 30.

By unlocking the locking pin 30, the pivotable handle part 18 and thus the siding part 14, which is engaged with the latter, is able to move in the proximal direction into a cleaning position beyond the end of the working stroke. In this cleaning position, the distal and proximal guidance means release the sliding part 14 in the manner described below, so that it can be lifted away from the shaft 10.

The distal guidance means consist of a guidance web 40 running axially, formed on the distal end of the shaft 10 and having a T-shaped cross-sectional profile. A guidance groove 49 runs axially on the distal end of the sliding part 14 and extends around the guidance web 40 having a corresponding T-shaped cross-sectional profile. As long as the sliding part 14 is moving in the axial area of the working stroke, the sliding part 14 is guided so that, due to the intermeshing of the guidance web 40 and the guidance groove 42, it is axially movable on the shaft 10 and is held in a form-fitting manner, preventing transverse movement in the sliding plane 28 and also preventing it from lifting away from the shaft 10. On the proximal end of the guidance web 40, its web head having a T-shaped enlarged shape is removed. In the cleaning position, the sliding part 14 becomes engaged in a form-fitting manner with the guidance groove 42 in this proximal area of the guidance web 40 and thus becomes disengaged from the form-fitting engagement in the direction perpendicular to the sliding plane 28. The distal end of the sliding part 14 can therefore be lifted away from the shaft 10 perpendicular to the sliding plane 28.

Figure 5:
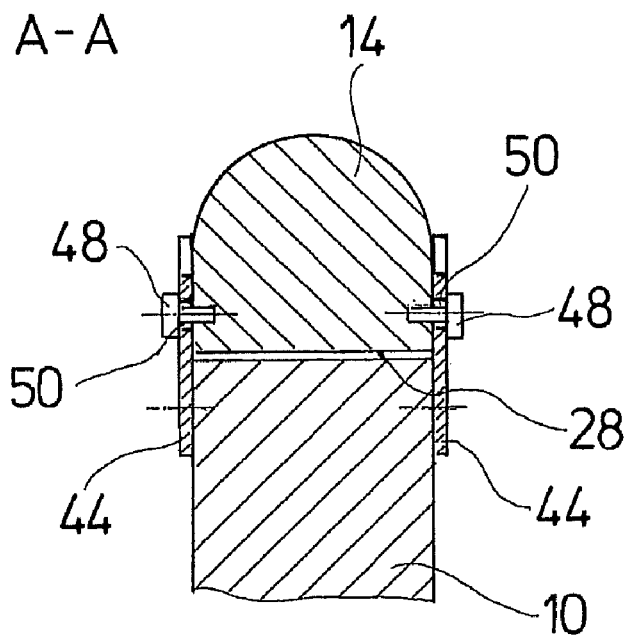
FIG. 5 shows a cross section through the proximal guidance in the working position according to section A-A in FIG. 1.
Figure 6:
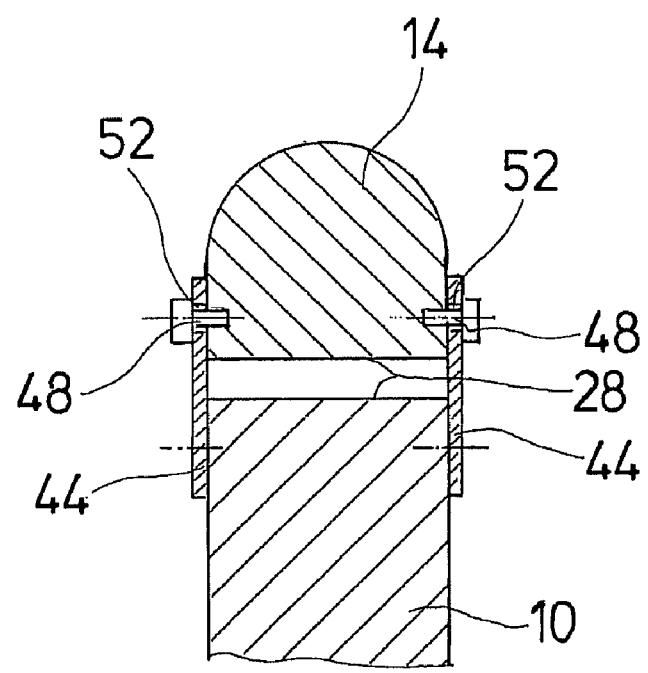
FIG. 6 shows a corresponding cross section through the proximal guidance means in the cleaning position according to section B-B in FIG. 3.

The proximal guidance means have two walls 44, which are mounted on the proximal end of the shaft 10 on both of its exterior surfaces. The walls 44 may be integrally molded in one piece with the shaft 10 or attached by screws or welding. The walls 44 protrude laterally on the shaft 10 beyond the sliding plane 28 and are thereby in contact with the exterior lateral faces of the sliding part, as can be seen in FIGS. 5 and 6 in particular. The walls 44 therefore hold the sliding part 14 axially displaceably and guided against a transverse displacement in the sliding plane 28 on the shaft. A link slot 46 is formed in the portion of the walls 44 protruding beyond the sliding plane 28. A pin 48, which is arranged in the sliding part 14 and protrudes transversely beyond its side walls, is guided in the link slots 46 in the walls 44. The link slots 46 each have a distal guidance section 50 running parallel to the sliding plane 28 in the axial direction. The spacing of the guidance section 50 from the sliding plane 28 and the distance of the pins 48 from the sliding plane are such that the sliding part 14 and the shaft 10 are in contact with one another in the sliding plane 28 when the pins 48 are each sitting in the guidance sections 50 of the walls 44. The length of the guidance section 50 of the link slots 46 in the axial direction is such that the pins 48 each move in these guidance sections 50 when the sliding part 14 is within its axial working stroke.

On the proximal end of the link slot 46, the guidance section 50 develops into an end section 52, which is angled away from the sliding plane 28. If the locking pin 30 is in the locking position, this limits the displacement of the sliding part 14 in the proximal direction to the working stroke, and the pins 48 are held in the respective guidance section 50 of the link slot 46 and cannot enter the end section 52. If the locking pin is unlocked, the pivotable handle part 18 may displace the sliding part 14 into the cleaning position beyond the working stroke under the influence of the expanding spring 20 in the proximal direction, whereupon the pins 48 each enter the end section 52 of the link slots 46. Since the end section 52 is angled away from the sliding plane 28, the pins 48 and, with them, the proximal end of the sliding part 14 move away from the sliding plane 28 of the shaft 10, and the proximal end of the sliding part 14 is lifted away from the shaft 10, as illustrated in FIG. 6. When, after unlocking the locking pin 30, the pivotable handle part 18 is pivoted further away from the fixed handle part 12, the shaft end of the pivotable handle part 18 protruding beyond the pivot pin 16 moves on a circular arc in the proximal direction, thereby releasing the driving pin 24 from the fork-shaped notch 22 in the pivotable handle part 18 in the proximal direction.

Figure 2:
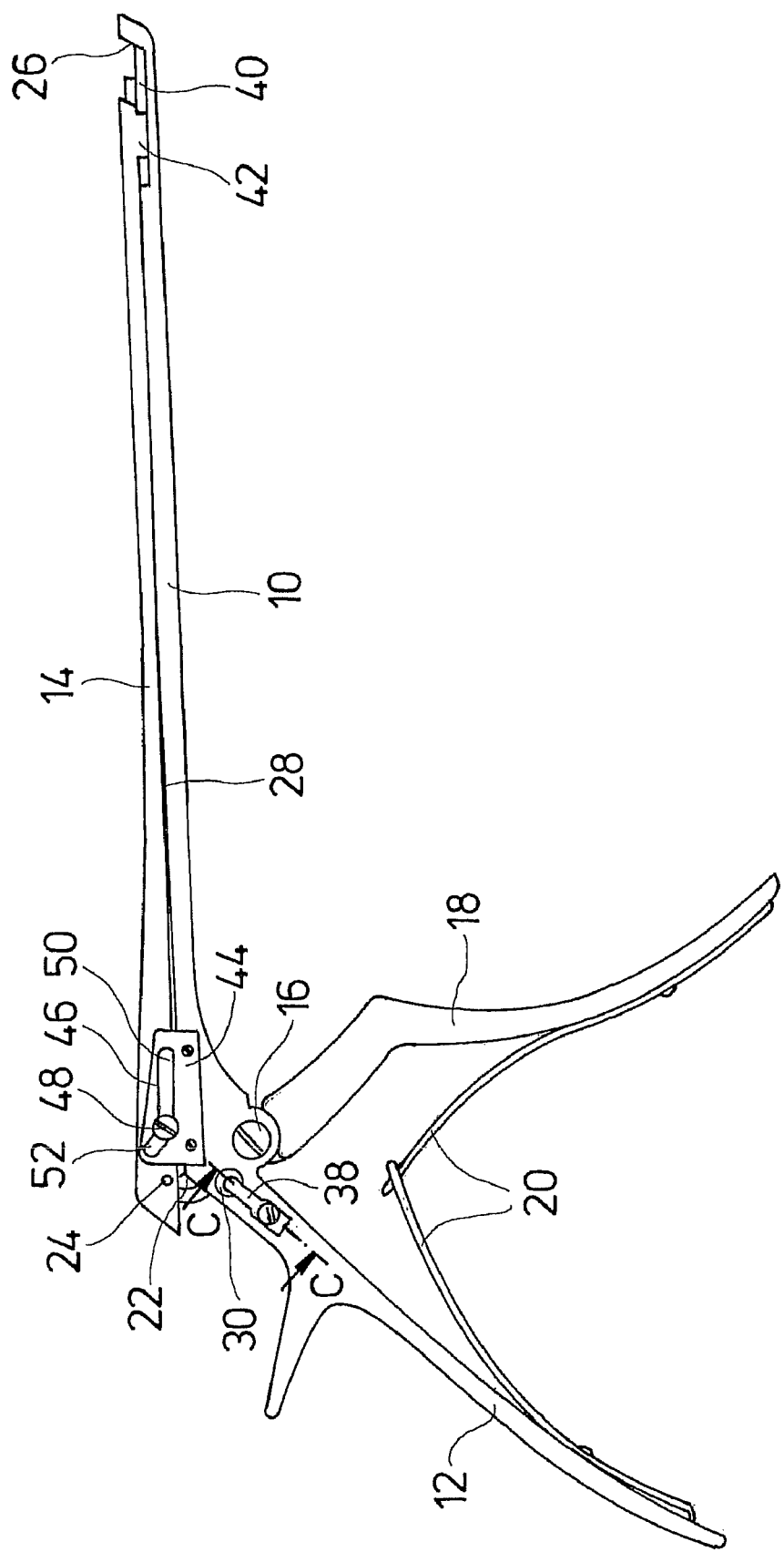
FIG. 2 shows a corresponding view of the opposite side of the instrument of FIG. 1.

FIGS. 1 and 2 show the instrument in the working position. The distal guidance means, i.e., the guidance web 40 and the guidance groove 42, are engaged, and the pins 48 of the sliding part 14 are in the guidance section 50 of the link slot 46 of the walls 44. The locking means formed by the locking pin 30 are in the locking position. In this working position, the sliding part 14 can be displaced axially on the shaft 10 within the working stroke by compression of the handle parts 12 and 18 against the action of the expanding spring 20, to thereby activate the working elements formed by the cutting edges 26. The sliding part 14 is axially displaceable here but is guided transversely to the axial direction in a form-fitting engagement on the shaft 10.

Figure 3:
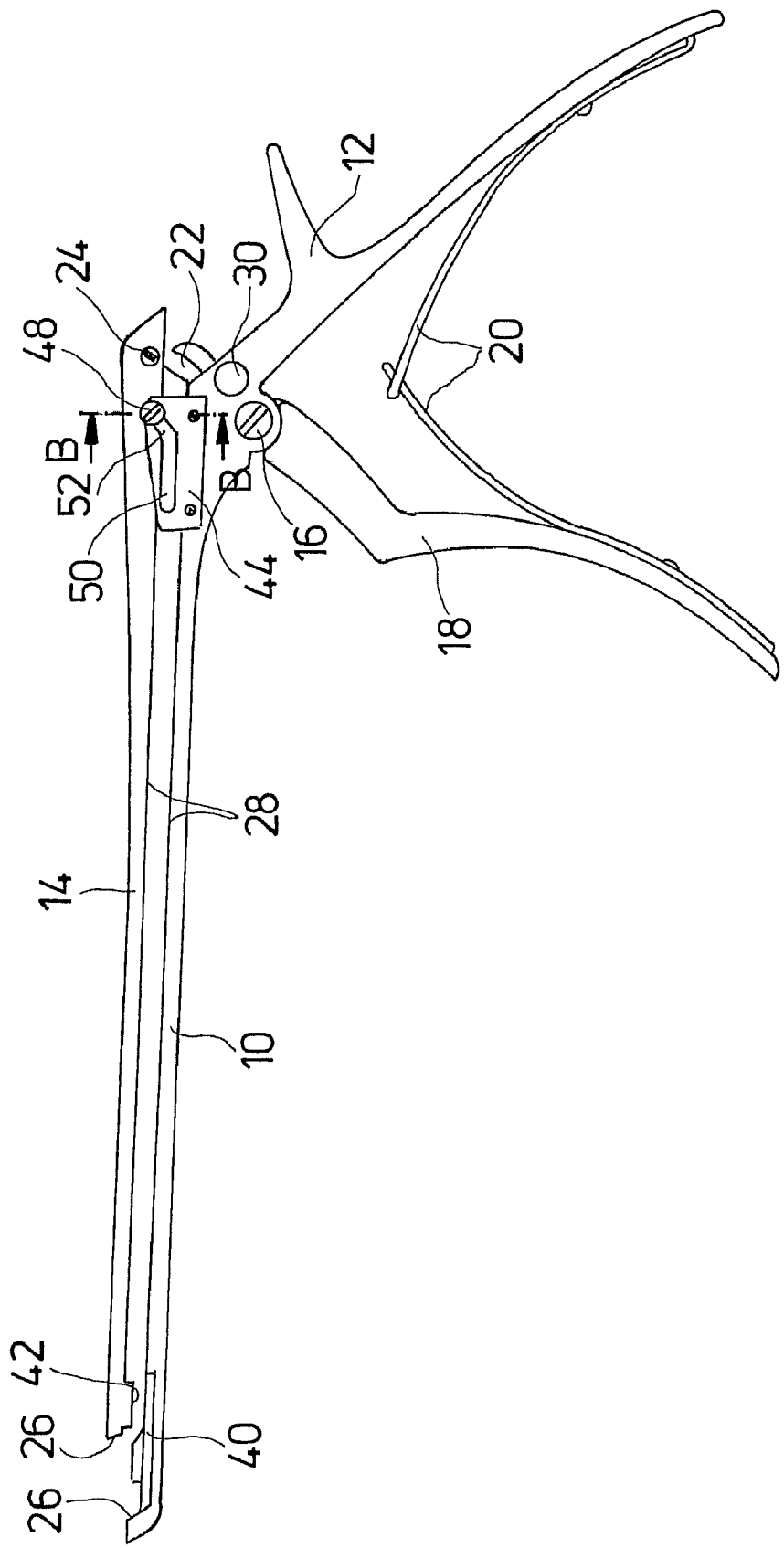
FIG. 3 shows a side view of the instrument of FIG. 1 in the cleaning position.

When the locking pin 30 is unlocked, the pivotable handle part 18 can pivot further under the action of the expanding spring 20, and the sliding part 14 can move into the cleaning position in the proximal direction. The distal guidance means here become disengaged, and the pins 48 of the sliding part 14 move into the end section 52 of the link slot 46. The sliding part 14 is thereby raised away from the shaft 10 over its entire axial length. The driving pin 24 of the sliding part 14 is released from the fork-shaped notch 22 in the pivotable handle part 18. This position is illustrated in FIG. 3.

Figure 4:
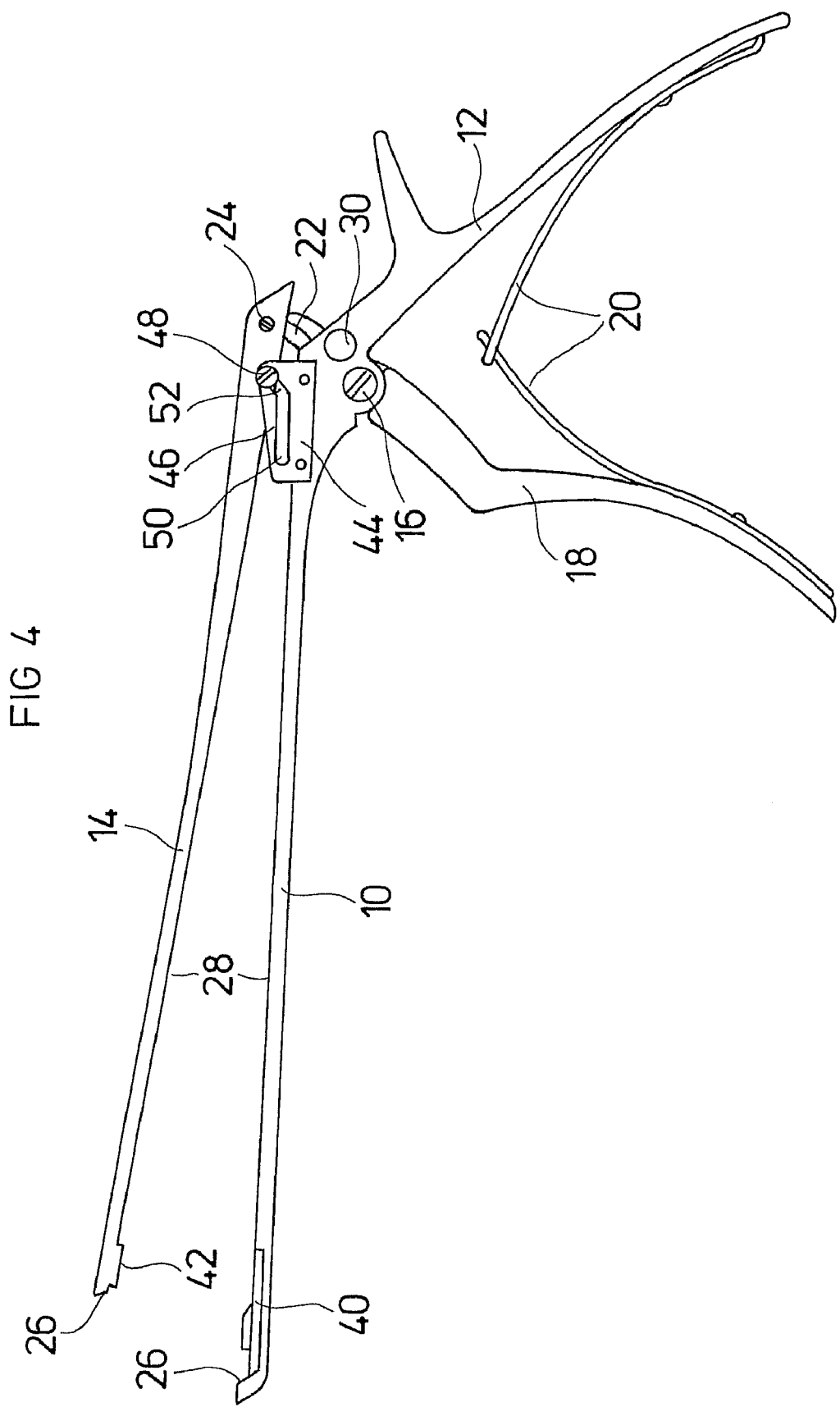
FIG. 4 shows a side view of the instrument of FIG. 1 in the cleaning position with the sliding part pivoted away.

The sliding part 14 can now be pivoted away from the shaft 10, whereby the pins 48 which are in the end sections 52 of the walls 44 serve as a pivot axis. This pivoting upward of the sliding part 14 about the proximal pivot axis of the pins 48 is illustrated in FIG. 4. In this position, the instrument can be cleaned, with the shaft 10 and the sliding part 14 readily accessible for the cleaning. However, the sliding part 14 remains inseparably connected to the remaining instrument by means of the pins 48 engaging in the link slot 46 of the walls 44.

If a complete separation of the sliding part 14 from the remaining instrument should be desired, this option can also be implemented easily. It is readily apparent that to do so, only the end sections 52 of the link slots 46 must be open on their proximal end. Then the pins 48 can be moved out of the link slots 46 in the proximal direction, so that the sliding part 14 is separated completely from the remaining instrument. Conversely, the pins 48 are again inserted into the link slots 46 for assembly of the cleaned instrument.

FIGS. 8 through 11 illustrate a second embodiment of the locking means which an limit the working stroke and can be unlocked to move the sliding part 14 beyond the proximal end of the working stroke into the cleaning position. Moreover, the instrument corresponds to the embodiment illustrated in FIGS. 1 to 6, which are described above.

Figure 10:
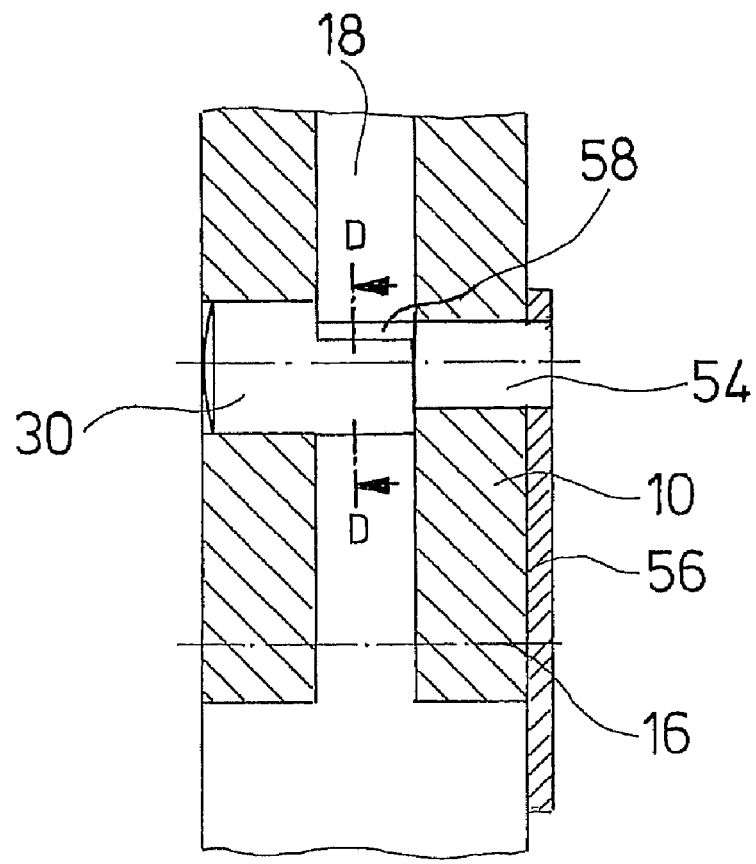
FIG. 10 shows a diagram of the locking means in the second embodiment corresponding to FIG. 7.

In the second embodiment of the locking means, a locking pin 30 is mounted in the fixed handle part 12 across the pivoted plane of pivotable handle part 18. The locking pin 30 is arranged proximally behind the end of the pivotable handle part 18 protruding beyond the pivot pin 16 on the shaft end. The locking pin 30 is rotatable about its axis but is mounted axially undisplaceably in the fixed handle part 12. As FIG. 10 shows, the locking pin 30 is therefore inserted from one side into a bore in the shaft 10 and/or the fixed handle part 12 and passes through this bore with a larger diameter and passes through the pivot distance of the pivotable handle part 18 formed like a link slot in the fixed handle part 12. On the opposite side of the shaft 10 and/or of the fixed handle part 12, the locking pin 30 with a section 54 of a reduced diameter passes through a bore in the shaft 10 and/or in the fixed handle part 12 with a reduced diameter accordingly. The locking pin 30 is therefore supported against an axial displacement toward the right in FIG. 10. On the end of the section 54 of the locking pin 30 protruding beyond the side surface of the shaft 10 and/or of the fixed handle part 12, a pivot lever 56 is attached, by means of which the locking pin 30 is secured against an axial displacement toward the left in FIG. 10.

Figure 11:
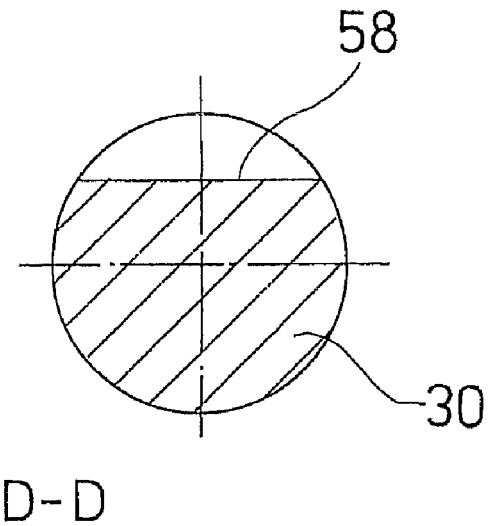
FIG. 11 shows a section through the locking means of the second embodiment according to sectional line D-D in FIG. 10.

In the central axial area of the locking pin 30, which in the pivot path of the pivotable handle part 18, the locking pin 30 is flattened in a circumferential angular area between 90° and 180°, e.g., of approx. 120°, as illustrated in FIG. 11. This yields a secant area 58 having a reduced radius in comparison with the larger radius of the locking pin 30.

The pivot lever 56 is formed by a plate spring which protrudes at a right angle away from the locking pin 30 and is in elastic spring contact with the exterior of the fixed handle part 12. A protrusion 60 protruding toward the fixed handle part 12 is pressed in on the free end of the pivot lever 56. A recess 62 whose distance from the locking pin 30 corresponds to the radial distance of the protrusion 60 from the locking pin 30, is cut in the exterior side face of the fixed handle part 12.

Figure 8:
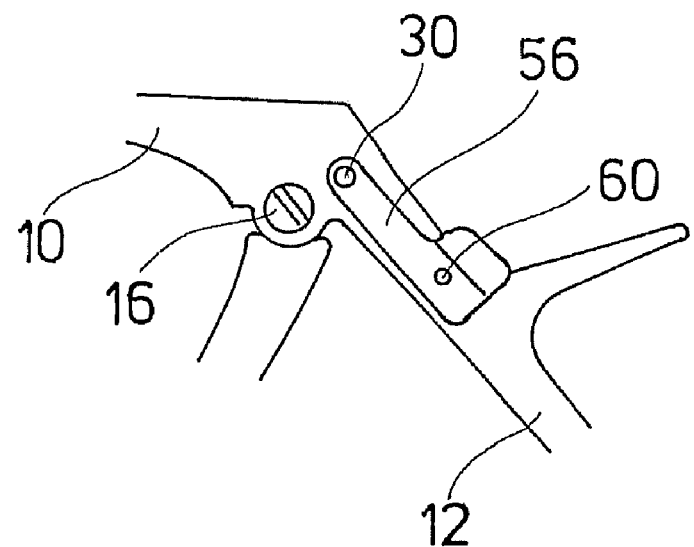
FIG. 8 shows detail of a side view of the instrument with a second embodiment of the locking means in the working position.
Figure 9:
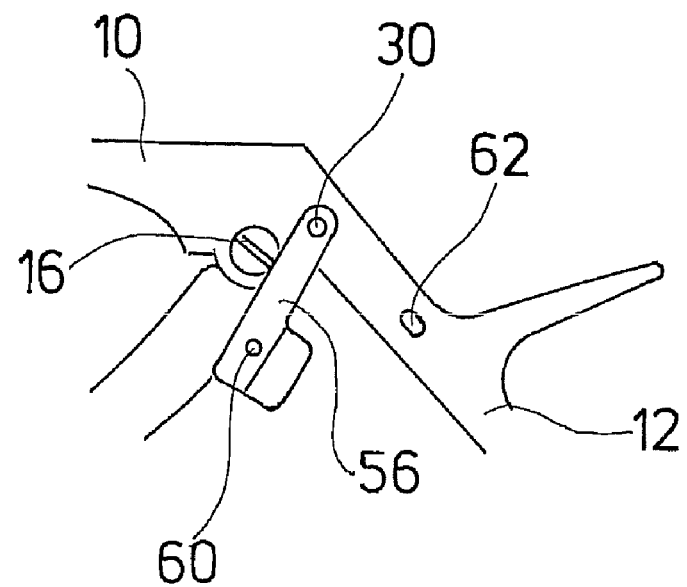
FIG. 9 shows a corresponding detail with the locking means of the second embodiment in the cleaning position.

While the instrument is in use, the sliding part 14 is situated in the area of its working stroke. The locking pin 30 is rotated into its locking position by means of the pivot lever 56. In this locking position, the circumferential angular range of the locking pin 30 having the larger radius is directed toward the pivotable handle part 18. The locking pin 30 thereby limits the pivot path of the pivotable handle part 18 with its larger diameter serving as a stop, so that the sliding part 14 cannot move beyond the proximal end of the working stroke. In this locking position the pivot lever 56 is contact with the exterior of the fixed handle part 12 and engages with its protrusion 60 in the recess 62 in a resilient manner, as illustrated in FIG. 8. The locking pin is thereby reliably held in the locking position and unintentional unlocking during use of the instrument is prevented. To clean the instrument, the pivot lever 56 is pivoted out of its spring catch position into the final locking position shown in FIG. 9. Through this pivoting movement, the locking pin 30 is rotated so that now its secant area 58 having the smaller radius is directed toward the pivotable handle part 18. The pivotable handle part 18 can now be spread by a further pivot path away from the fixed handle part 12, which results from the difference in radius between the locking pin 30 and the flattened secant area 58. The secant area 58 having the smaller radius then limits the pivot angle of the pivotable handle part 18. Due to this further pivoting of the handle part 18, the sliding part 14 is moved in the proximal direction into the cleaning position beyond the end of the working stroke; in this position, the sliding part 14 is released from the shaft 10 and can be lifted away from it.

In the claims, means- or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A surgical instrument, said surgical instrument comprising a shaft on whose proximal end is arranged a fixed handle part, said shaft further comprising:
   (a) a sliding part, said sliding part further comprising:
      (i) a pivotable handle part mounted pivotably with respect to said fixed handle part, said pivotable handle part for axially moving said sliding part; and
      (ii) guidance means for guiding said sliding part on said shaft while in contact with said shaft in a sliding plane within an axial working stroke, said guidance means further comprising:
         (1) a distal guidance means portion of said guidance means; and
         (2) a proximal guidance means portion of said guidance means, said proximal guidance means further comprising two walls, wherein said two walls are arranged so that:
            (A) said two walls are axially parallel on the exteriors of said shaft and said sliding part and which guide said sliding part with respect to a transverse displacement in said sliding plane on said shaft; and
            (B) a link slot is formed in each wall;
   (b) locking means, said locking means limiting the axial displacement of said sliding part on a proximal end of said axial working stroke, and after unlocking said locking means, said sliding part being movable beyond said proximal end of said axial working stroke into a cleaning position in which said distal guidance means are disengaged, so that said sliding part can be lifted away from said shaft;
   (c) a pin, said pin engaging in said each link slot to guide said sliding part; each link slot having a guidance section running parallel to said sliding plane, such that said sliding part is held in contact with said shaft within said working stroke due to the axial length of said guidance section and due to the distance of said guidance section and said pin from said sliding plane; and (d) an end section, wherein said end section is connected to said guidance section of said each link slot into which said corresponding pin enters in said cleaning position of said sliding part and which makes it possible to lift said proximal end of said sliding part away from said shaft.

2. The surgical instrument according to claim 1, wherein said two walls are arranged laterally on said shaft, and wherein said sliding part is displaceable between said two walls, and said each pin is arranged on said sliding part.

3. The surgical instrument according to claim 2, wherein said end section is connected proximally to said guidance section of the respective said link slot.

4. The surgical instrument according to claim 3, wherein said each end section is open proximally, so that said each pin can come out of the respective said link slot in the proximal direction, so that said sliding part is separated from said shaft.

5. The surgical instrument according to claim 3, wherein said each end section is closed proximally and is angled upward and away from said sliding plate, so that said sliding part is pivotable away from said shaft about said each pin, which is in said end section, as the pivot axis, but remains connected to said shaft.

6. The surgical instrument according to claim 1, wherein said pivotable handle part comprises a fork-shaped end extending around a driving pin of said sliding part when said sliding part is proximate said working stroke; and after unlocking said locking means, said end of said pivotable handle part is pivotable in the proximal direction to such an extent that said driving pin is movable out of said fork-shaped end in said proximal direction.

7. The surgical instrument according to claim 1, wherein: said distal guidance means further comprises:

an axial guidance web having a T-shaped profile cross section, which engages in a guidance groove with a corresponding T-shaped profile cross section in the range of said working stroke.

8. The surgical instrument according to claim 1, wherein: said locking means comprises:

a locking pin, which is mounted to be transversely displaceable in said shaft and/or in said fixed handle part and is within the pivot range of said pivotable handle part;

said locking pin has a first axial section with a larger diameter and a second axial section with a smaller diameter; and in the locking position;

said first axial section having the larger diameter limits the pivot angle of said pivotable handle part as a stop, and in the unlocking position, said second axial section having the smaller diameter limits said pivot angle.

9. The surgical instrument according to claim 1, wherein: said locking means comprises a locking pin;

said locking pin being arranged across said pivot plane in the pivot range of said pivotable handle part in said shaft and/or said fixed handle part, such that said locking pin has two circumferential angular ranges, each having a different radius; and said locking pin is mounted rotatably about its axis in such a manner that in the locking position, the circumferential angular range having the larger radius, limits the pivot angle of said pivotable handle part as a stop, and in the unlocked position, the circumferential angular range having the smaller radius limits said pivot angle.

10. The surgical instrument according to claim 9, wherein said circumferential angular range having the smaller radius is formed by a secant area of said circular cross section of said locking pin.

11. The surgical instrument according to claim 9, wherein said locking pin is rotatable by means of a pivot lever which engages in the locking position on said fixed handle part in a resilient manner.

12. A surgical instrument, said surgical instrument comprising:

a shaft on whose proximal end is arranged a fixed handle part, said shaft further comprising:

(a) a sliding part, said sliding part further comprising:
(i) a pivotable handle part mounted pivotably with respect to said fixed handle part, said pivotable handle part for axially moving said sliding part; and
(ii) guidance means for guiding said sliding part on said shaft while in contact with said shaft in a sliding plane within an axial working stroke, said guidance means further comprising:
(1) a distal guidance means portion of said guidance means, wherein said distal guidance means further comprises an axial guidance web having a T-shaped profile cross section, which engages in a guidance groove with a corresponding T-shaped profile cross section in the range of said working stroke.
(2) a proximal guidance means portion of said guidance means, said proximal guidance means further comprising two walls, wherein said two walls are arranged so that:
(A) said two walls are axially parallel on the exteriors of said shaft and said sliding part and which guide said sliding part with respect to a transverse displacement in said sliding plane on said shaft; and
(B) a link slot is formed in each wall;

(b) locking means, said locking means limiting the axial displacement of said sliding part on a proximal end of said axial working stroke, and after unlocking said locking means, said sliding part being movable beyond said proximal end of said axial working stroke into a cleaning position in which said distal guidance means are disengaged, so that said sliding part can be lifted away from said shaft;

(c) a pin, said pin engaging in said each link slot to guide said sliding part; each link slot having a guidance section running parallel to said sliding plane, such that said sliding part is held in contact with said shaft within said working stroke due to the axial length of said guidance section and due to the distance of said guidance section and said pin from said sliding plane; and (d) an end section, wherein said end section is connected:
(i) to said guidance section of said each link slot into which said corresponding pin enters in said cleaning position of said sliding part and which makes it possible to lift said proximal end of said sliding part away from said shaft; and
(ii) proximally to said guidance section of the respective said link slot.

13. A surgical instrument according to claim 12, wherein said each end section is open proximally, so that said each pin can come out of the respective said link slot in the proximal direction, so that said sliding part is separated from said shaft.

14. A surgical instrument according to claim 12, wherein said each end section is closed proximally and is angled upward and away from said sliding plate, so that said sliding part is pivotable away from said shaft about said each pin, which is in said end section, as the pivot axis, but remains connected to said shaft.

15. A surgical instrument, according to claim 12 wherein said pivotable handle part comprises a fork-shaped end extending around a driving pin of said sliding part when said sliding part is proximate said working stroke; and
    after unlocking said locking means, said end of said pivotable handle part is pivotable in the proximal direction to such an extent that said driving pin is movable out of said fork-shaped end in said proximal direction.

16. A surgical instrument, according to claim 12 wherein: said locking means comprises:
    a locking pin, which is mounted to be transversely displaceable in said shaft and/or in said fixed handle part and is within the pivot range of said pivotable handle part;
    said locking pin has a first axial section with a larger diameter and a second axial section with a smaller diameter; and in the locking position;
    said first axial section having the larger diameter limits the pivot angle of said pivotable handle part as a stop, and in the unlocking position, said second axial section having the smaller diameter limits said pivot angle.

17. A surgical instrument, according to claim 12 wherein: said locking means comprises a locking pin;
    said locking pin being arranged across said pivot plane in the pivot range of said pivotable handle part in said shaft and/or said fixed handle part, such that said locking pin has two circumferential angular ranges, each having a different radius; and
    said locking pin is mounted rotatably about its axis in such a manner that in the locking position, the circumferential angular range having the larger radius, limits the pivot angle of said pivotable handle part as a stop, and in the unlocked position, the circumferential angular range having the smaller radius limits said pivot angle.

18. A surgical instrument, said surgical instrument comprising a shaft on whose proximal end is arranged a fixed handle part, said shaft further comprising:
    (a) a sliding part, said sliding part further comprising:
    (b) a pivotable handle part mounted pivotably with respect to said fixed handle part, said pivotable handle part for axially moving said sliding part; and
    (c) guidance means for guiding said sliding part on said shaft while in contact with said shaft in a sliding plane within an axial working stroke, said guidance means further comprising:
       (i) a distal guidance means portion of said guidance means; and
       (ii) a proximal guidance means portion of said guidance means, said proximal guidance means further comprising two walls, wherein said two walls are axially parallel on the exteriors of said shaft and said sliding part and which guide said sliding part with respect to a transverse displacement in said sliding plane on said shaft, and a link slot is formed in each wall;
    (d) locking means, said locking means limiting the axial displacement of said sliding part on a proximal end of said axial working stroke, and after unlocking said locking means, said sliding part being movable beyond said proximal end of said axial working stroke into a cleaning position in which said distal guidance means are disengaged, so that said sliding part can be lifted away from said shaft;
    (e) a pin, said pin engaging in said each link slot to guide said sliding part; and
    (f) an end section, wherein said end section is connected to said guidance section of said each link slot into which said corresponding pin enters in said cleaning position of said sliding part.

* * * * *